US007810493B2

(12) United States Patent
Resnick

(10) Patent No.: US 7,810,493 B2
(45) Date of Patent: Oct. 12, 2010

(54) DRINK TUBE SYSTEM FOR RESPIRATORY PROTECTIVE DEVICE

(75) Inventor: Todd A. Resnick, Stuart, FL (US)

(73) Assignee: TMR-E, LLC, Tampa, FL (US)

( * ) Notice: Subject to any disclaimer, the term of this patent is extended or adjusted under 35 U.S.C. 154(b) by 942 days.

(21) Appl. No.: 11/551,068

(22) Filed: Oct. 19, 2006

(65) Prior Publication Data

US 2008/0093399 A1 Apr. 24, 2008

(51) Int. Cl.
*A61M 15/00* (2006.01)
*A62B 7/00* (2006.01)

(52) U.S. Cl. ............................ 128/202.15; 128/202.13; 128/201.28

(58) Field of Classification Search ............ 128/202.15, 128/202.13, 201.28, 204.27; 224/148.2
See application file for complete search history.

(56) References Cited

U.S. PATENT DOCUMENTS

| | | | | |
|---|---|---|---|---|
| 1,366,437 | A | 1/1921 | Wagenhorst | |
| 2,023,267 | A | 12/1935 | De Saint Rapt et al. | |
| 3,635,217 | A * | 1/1972 | Potash | 128/201.19 |
| 3,645,261 | A * | 2/1972 | West | 128/201.19 |
| 6,758,213 | B1 * | 7/2004 | Brekken | 128/202.15 |
| 2004/0155054 | A1 * | 8/2004 | McKitrick | 222/1 |

* cited by examiner

*Primary Examiner*—Justine R Yu
*Assistant Examiner*—Colin Stuart
(74) *Attorney, Agent, or Firm*—Design IP

(57) ABSTRACT

A retractable drink system for providing fluid delivery to a wearer with a donned protective mask covering the mouth, the drink system including a drink tube mounted within the interior of the mask, the drink tube having a retracted position and a deployed position; and an actuation coupling externally accessible with respect to the mask, the actuation coupling moving the drink tube between the retracted and deployed positions.

5 Claims, 3 Drawing Sheets

DRINK TUBE SYSTEM FOR RESPIRATORY PROTECTIVE DEVICE

FIELD OF INVENTION

This invention relates to a respiratory protective device and particularly to a retractable drink tube system for delivery of fluid to the wearer while the hood is donned.

BACKGROUND OF THE INVENTION

Respiratory protective devices are only effective if they are worn. In many situations, wearers of the protective devices must don them for extended periods of time. While respiration is a critical physiological need, so is hydration and nutrition. Some respiratory protective devices have no provision for introducing fluids to the wearer while the device is donned. Thus, the device must either be removed—thereby sacrificing protection, or the wearer must suffer thirst and hunger until the threat passes.

Some protective masks do provide a drink tube which, when coupled with an external fluid supply, permit the wearer to consume liquids. However, current designs have a number of drawbacks. First, the tubes are fixed in proximity to the wearer's mouth. While this facilitates use of the drink tube, it is also uncomfortable and/or distracting to a wearer that dons the protective mask for a period of time. The drink tube is inherently an obstruction to the user when not needed. Because the tube is fixed, they are generally required to be made of soft, flexible material as they come into frequent contact with the mouth, face and possibly nose of the wearer. The soft, flexible material often collapses under the vacuum created by the user to draw in a volume of liquid, particularly if it is viscous. In addition, because the material is soft and yielding, the internal diameter of the drink tube is restricted or the tube will collapse and/or kink.

What is needed in the art is a drink tube that pivots from a retracted and deployed position so that the wearer is only presented with the obstruction when needed.

Another need in the art is a drink tube that can be actuated without removing the respiratory protective device thereby maintaining constant protection for the wearer.

Another need in the art is for a drink tube that does not collapse or kink.

Another need in the art is for a drink tube that supports a larger internal diameter to permit greater amounts of fluid to be consumed by the wearer without the resistance inherent with a smaller internal diameter drink tube.

Another need in the art is for a drink tube that is adjustable to different positions within the protective mask to accommodate an individual user's preferences and/or physiology.

SUMMARY OF INVENTION

The present invention is a retractable drink system that provides fluid delivery to a wearer of a donned protective mask that covers the mouth. Fluid is generally defined as any substance such as a gas, liquid or powder which flows. It differs from a solid in that is can offer no permanent resistance to the change of shape. For the purposes of the present application fluids may include, but are not limited to, hydrating liquids such as water, liquid food solutions for caloric intake, and medical/therapeutic substances. In the context of this application, a mask includes those devices used to create a substantially fluid-tight seal about the mouth. Masks include, but are not limited to, full face piece masks, half masks, nose cups and quarter masks. The fluid tight seal may be set against airborne contaminants such as nuclear, chemical and/or biological particles, or may set against the intrusion of liquids such as an underwater mask. The mask may be directly exposed to the hazardous environment or may be further protected by another barrier such as a hood or full-body suit.

A drink tube is mounted within the interior of the mask, the drink tube having a retracted position and a deployed position. An actuation coupling, externally accessible with respect to the mask, moves the drink tube between the retracted and deployed positions. The drink tube is biased towards a retracted position when the actuation coupling is not engaged. A fluid shut-off valve may be provided that is engaged when the drink tube is in a retracted position and disengaged when the drink tube is in a deployed position. In an embodiment of the invention, the drink tube moves from the retracted and deployed positions about a predetermined pivot point axis, the actuation coupling comprises an elongate member that is affixed to and turns in synchronization with the pivot point axis.

A fluid shut-off valve may be integrated into the drink tube system whereby when the drink tube is in a retracted position the shut-off valve is engaged. When the drink tube is in a deployed position the shut-off valve is disengaged. In another embodiment of the invention, an extendable drink tube may be provided comprising a plurality of fluid-tight tubes slideably received within each other to extend and retract along a longitudinal path.

An embodiment of the invention is well suited for nose cup masks. In this embodiment, a substantially triangular nose cup has a top nose bridge, a left lower corner, a right lower corner, a face-sealing concave rear side opening, a convex front, an interior and an exterior. A drink tube is mounted within the interior of the nose cup, the drink tube has a retracted position and a deployed position. An actuation coupling externally accessible with respect to the nose cup moves the drink tube between the retracted and deployed positions. An exhalation port extends through the nose cup front. A substantially rigid backing plate is mounted about the exhalation port on the interior surface of the nose cup front. The drink tube is pivotally affixed to the backing plate. A fluid supply inlet port passes through the backing plate. The fluid supply inlet ports fluidly couples a drink source external to the nose cup with the drink tube internal to the nose cup. An actuation coupling is externally accessible with respect to the nose cup, the actuation coupling moving the drink tube between the retracted and deployed positions wherein the drink tube moves from the retracted and deployed positions about a predetermined pivot point axis, the actuation coupling includes an elongate member that is affixed to and turns in synchronization with the pivot point axis. An attachment bracket pivotally secures a portion of the drink tube to the backing plate. The attachment bracket is secured to a first edge of the backing plate and the drink tube in the retracted position laterally traverses the backing plate thereby terminating at a second edge of the backing plate, the second edge substantially distal to the first edge. The drink tube traversing the backing plate may be preformed to align with the outer perimeter of the exhalation port thereby maintaining an unobstructed exhalation pathway.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
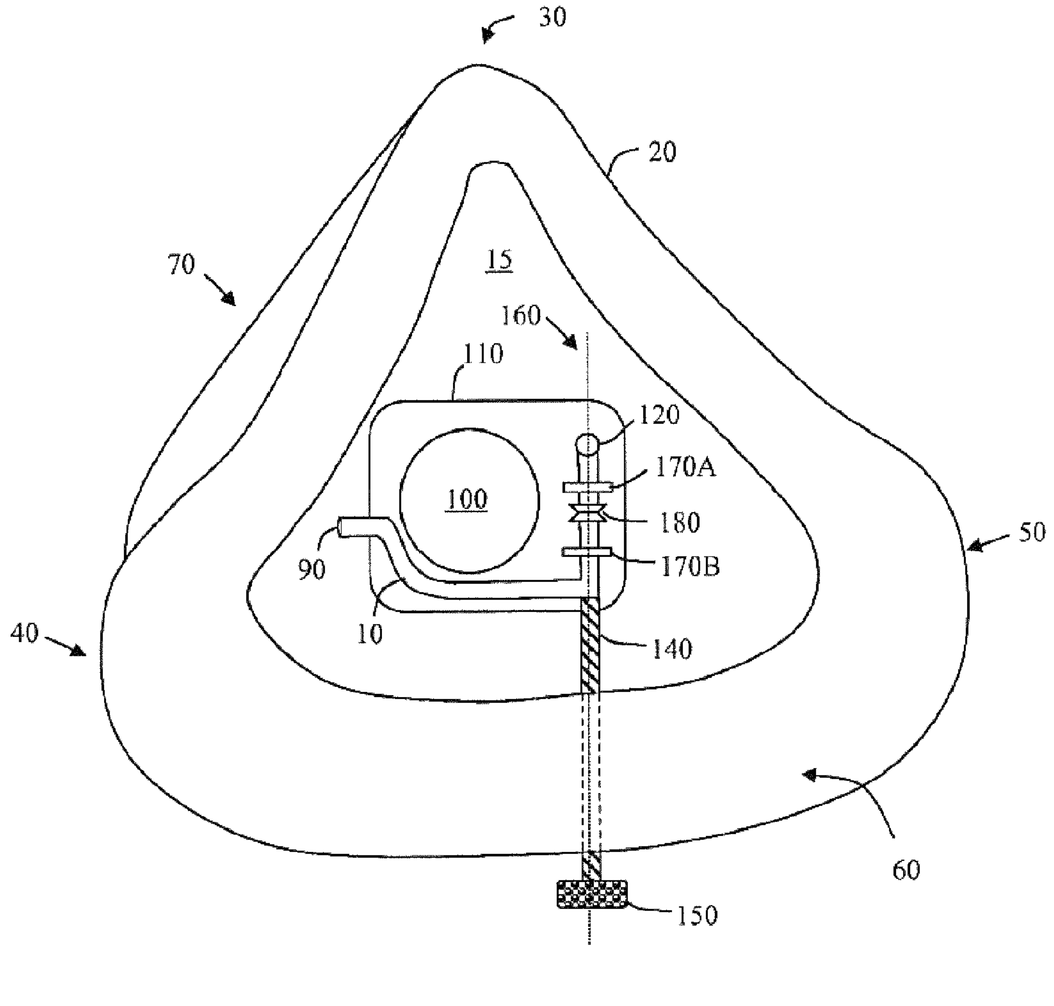
FIG. 1 is an elevated view of a nose cup embodiment of the invention.

Turning to FIG. 1, an exemplary embodiment of the invention integrates the pivoting drink tube 10 within the interior 15 of nose cup 20. Nose cup 20 is substantially triangular in shape with a top nose bridge 30, a left lower corner 40, a right lower corner 50, a face-sealing concave rear side opening 60, and convex front 70. Drink tube 10 couples fluid supply source 130 (FIGS. 2A-B) with dispensing tip 90. Exhalation port 100 extends through nose cup front 70. Substantially rigid backing plate 110 is mounted about exhalation port 100 on the interior surface of nose cup front 70.

Fluid supply inlet port 120 passes through backing plate 110. Fluid supply inlet port 120 fluidly couples fluid source 130 (FIGS. 2A-B) external to nose cup 20 with drink tube 10 internal to nose cup 20. Actuation coupling 140 is externally accessible with respect to nose cup 20 via actuation interface 150.

Figure 2A:
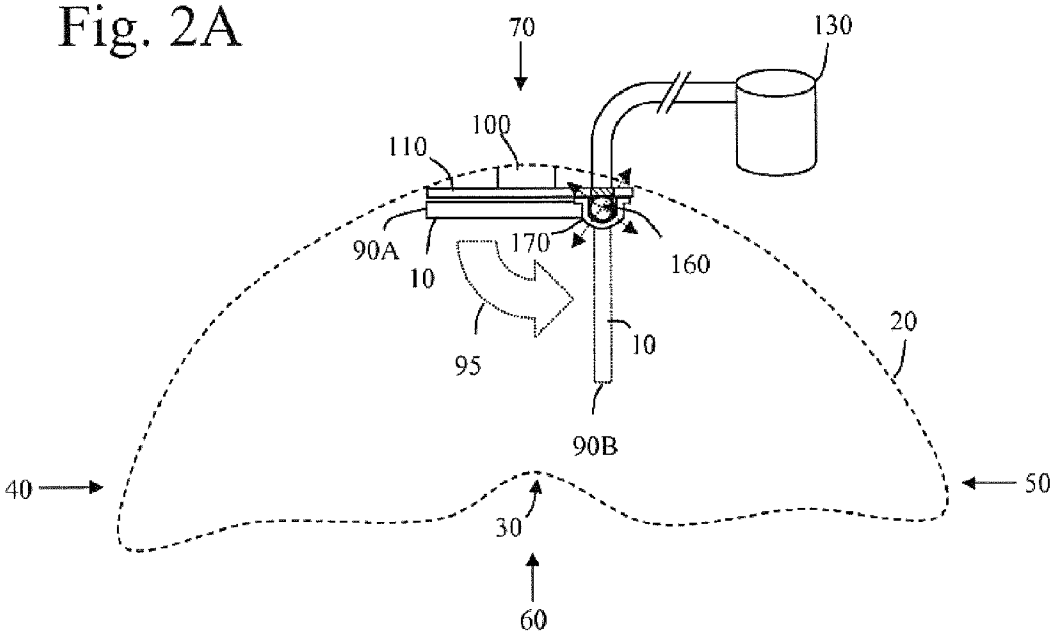
FIGS. 2A-2B are top down, partially sectional elevated views of a nose cup embodiment of the invention.
Figure 2B:
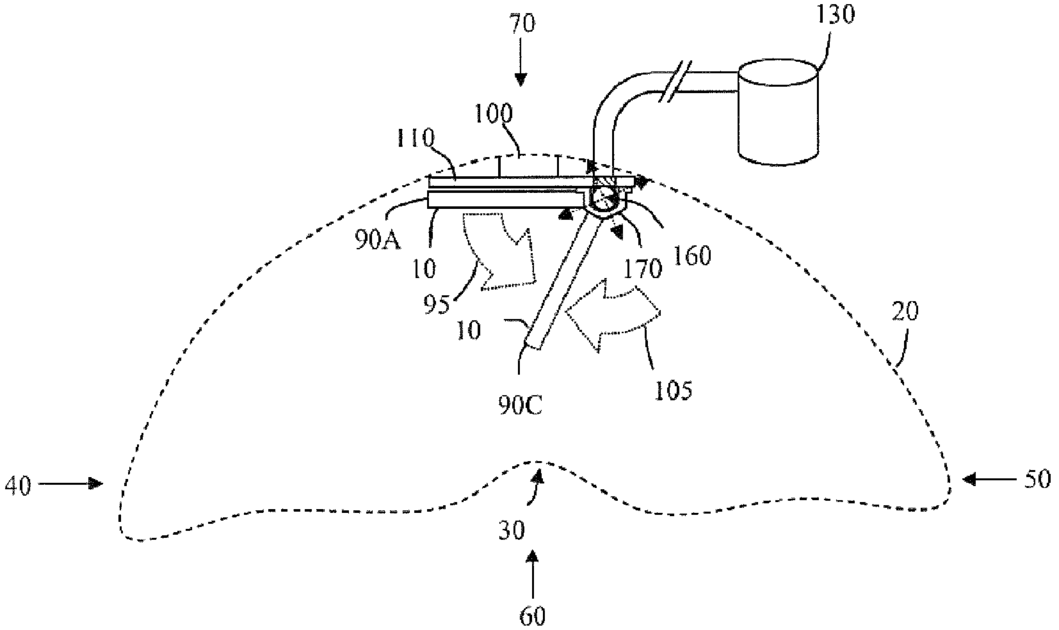

Turning to FIGS. 2A-B, actuation coupling 140 (FIG. 1) moves drink tube 10 from a refracted position to a deployed position along an arc. Note that retracted dispensing tip position 90A moves along the arc defined by arrow path 95 to deployed dispensing tip position 90B in FIG. 2A. In FIG. 2B, drink tube 10 is moved to a deployed position along arrow path 105. Note that deployed dispensing tip position 90C is further away from concave rear side opening 60 than dispensing tip position 90B. An advantage of the present invention is that the wearer can move drink tube 10 to a position that is most effective and comfortable to that particular wearer.

In the embodiment shown, actuation coupling 140 moves drink tube 10 from a retracted position to a deployed position about predetermined pivot point axis 160. At least one attachment bracket 170 pivotally secures a portion of drink tube 10 to backing plate 110. For pivoting a fluid connection, one or more pivot joints 180 may be provided along the pivot point axis 160.

It can be seen in FIG. 1 that attachment brackets 170A-B are secured to a first edge of backing plate 110. Drink tube 10 in the retracted position laterally traverses backing plate 110 thereby terminating at a second edge of the backing plate, the second edge substantially distal to the first edge. Drink tube 10 is also preformed to align with the outer perimeter of exhalation port 100 thereby maintaining an unobstructed exhalation pathway while in the retracted position. An advantage of this configuration is that drink tube 10, exhalation port 100 and backing plate 110 form a compact, rigid collection of parts around which nose cup 20 may be folded for compact storage.

Figure 3A:
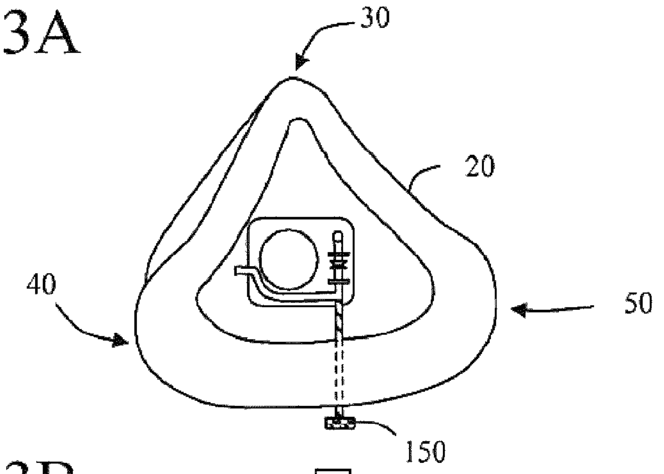
FIGS. 3A-3D are elevated sequential views of a nose cup folding method according to an embodiment of the invention.
Figure 3B:
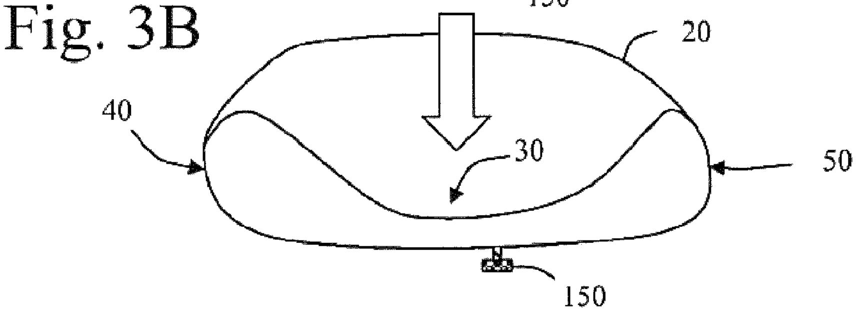
Figure 3C:
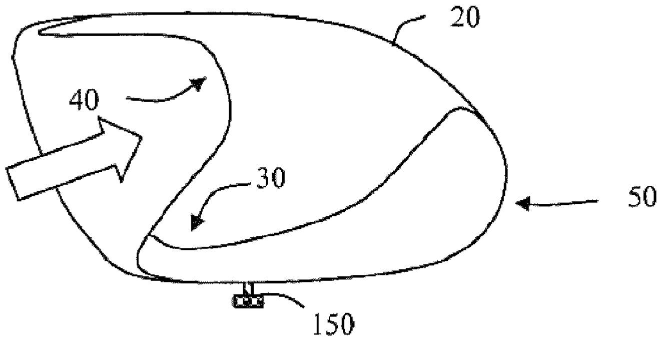
Figure 3D:
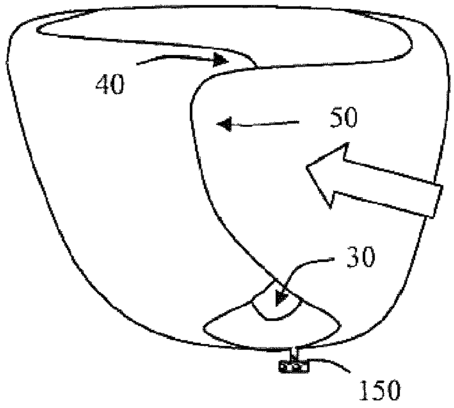

A folding method according to an embodiment of the invention is provided in FIGS. 3A-D. As noted above, nose cup 20 is generally triangular-shaped having a nose bridge 30, a left lateral extension 40 and a right lateral extension 50 (FIG. 3A). Nose bridge 30 is folded downward (FIG. 3B). Either lateral extension (left lateral extension 40 in this example) is folded inward over the folded nose bridge 30. (FIG. 3C) Finally, the remaining later extension (right lateral extension 50 in this example) is folded inward to either abut or overlap left lateral extension 40 thereby forming highly compact folded nose cup 30. Note that the position of actuation interface 50 disposed substantially below backing plate 110 does not obstruct the folding method.

An advantage of the invention is that by pivoting the drink tube away from the wearer when not in use, the drink tube can be made of substantially rigid material which permits a larger internal diameter, greater fluid flow, and less drinking resistance.

Another advantage of the invention is that the drink tube may be repositioned without removing the protective device thereby maintaining its protection factor.

Yet another advantage of the invention is that embodiments thereof support folding of the mask into highly compact shapes for storage and portability.

Yet another advantage of the invention is that it permits the wearer to adjust the position of the drink tube to accommodate the preferences, comfort and physiology of the wearer.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A respiratory protective device comprising a mask adapted to be worn by wearer thereof; said device characterized by a drink tube system comprising:

i. a fluid supply port that fluidly couples a fluid source located external to said mask with a rigid drink tube located internal to said mask;

ii. said rigid drink tube including a rigid and substantially straight upstream section having a longitudinal axis, said upstream section connected at a substantially 90 degree angle to a rigid downstream section, said downstream section terminating in a dispensing tip adapted to be grasped by the wearer's mouth;

iii. said upstream section adapted to rotate about said axis to effect conjoint movement of said dispensing tip between a retracted position when said dispensing tip is located away from the wearer's mouth, and a deployed position when said dispensing end is located proximate the wearer's mouth; and iv. an actuation interface located external to said mask, said interface adapted to rotate an actuation coupling that is connected to, and disposed in axial alignment with, said upstream section such that rotation of said actuation coupling effects conjoint rotation of said upstream section about its longitudinal axis.

2. A respiratory protective device comprising:

a. a mask adapted to be worn by wearer thereof;

b. an exhalation port extending through said mask;

c. a substantially rigid backing plate mounted about said exhalation port and secured to an interior surface of said mask;

d. said backing plate having a front side facing away from the wearer and a back side facing toward the wearer;

e. said back side having a surface area along its perimeter, said surface area including a first edge and a second edge that meet at a substantially 90 degree angle;

said device characterized by a drink tube system comprising:

i. a fluid supply port extending through said backing plate, said fluid supply port fluidly coupling a fluid source located external to said mask with a rigid drink tube disposed on said back side of said backing plate;

ii. said rigid drink tube comprising a rigid and substantially straight upstream section having a longitudinal axis, said upstream section connected at a substantially 90 degree angle to a rigid downstream section; said downstream section terminating in a dispensing tip adapted to be grasped by the wearer's mouth;

iii. said upstream section mounted along said first edge of said back side of said backing plate and adapted to rotate about said axis to effect conjoint movement of said downstream section between a retracted position when said downstream section is disposed adjacent to said second edge of said back side and said dispensing tip located away from the wearer's mouth, and a deployed position when said downstream section is disposed substantially normal to said back side and said dispensing tip located proximate the mouth of said wearer; and iv. an actuation interface located external to said mask, said interface adapted to rotate an actuation coupling that is connected to, and disposed in axial alignment with, said upstream section such that rotation of said actuation coupling effects conjoint rotation of said upstream section about its longitudinal axis.

3. The respiratory protective device of claim 2 wherein said first and second edge of said backside of said backing plate comprise, respectively, the right edge and the bottom edge of said back side when viewed from the wearer's perspective.

4. The respiratory protective device of claim 1 wherein said mask is selected from the group consisting of full face piece masks, half masks, nose cups and quarter masks.

5. The respiratory protective device of claim 1 wherein said mask comprises a nose cup having a top nose bridge, a left lateral extension, and a right lateral extension, and wherein said nose cup has a folded configuration comprising said nose bridge folded downward and said two lateral extensions folded inward.

* * * * *